(12) United States Patent
Aramata et al.

(10) Patent No.: US 6,339,167 B2
(45) Date of Patent: Jan. 15, 2002

(54) PROCESS FOR PREPARING ORGANOHALOSILANES

(75) Inventors: Mikio Aramata, Annaka; Kazutoshi Fujioka, Usui-gun; Masahiro Yuyama, Kashima-gun, all of (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/782,190

(22) Filed: Feb. 14, 2001

(30) Foreign Application Priority Data

Feb. 14, 2000 (JP) ............................................. 12-034646

(51) Int. Cl.$^7$ .................................................. C07F 7/16

(52) U.S. Cl. ...................................................... 556/472

(58) Field of Search .......................................... 556/472

(56) References Cited

U.S. PATENT DOCUMENTS 5,500,399 A * 3/1996 Faure et al. ................. 556/472
5,654,460 A * 8/1997 Rong .......................... 556/472

* cited by examiner

*Primary Examiner*—Paul F. Shaver
(74) *Attorney, Agent, or Firm*—Millen, White, Zelano & Branigan, P.C.

(57) ABSTRACT

Organohalosilanes are prepared by reacting metallic silicon with a halogenated hydrocarbon in the presence of a copper or copper compound catalyst and an activated aluminum, aluminum alloy or aluminum carbide promotor. The reaction is carried out at a temperature of 250–400° C. in a stirred tank reactor or a fluidized bed reactor. The inventive process shortens the time required for activation in the Rochow reaction and increases the selectivity for desirable diorganodihalosilanes. The steady state is thus prolonged and conversion of the silicon enhanced, resulting in an improved reaction performance.

9 Claims, No Drawings

PROCESS FOR PREPARING ORGANOHALOSILANES

BACKGROUND OF THE INVENTION

A process for preparing organohalosilanes from metallic silicon and halogenated hydrocarbons using a copper or copper compound catalyst was first disclosed in U.S. Pat. No. 2,380,995, and is today called the Rochow reaction after the name of the inventor. The silicone industry has carried out organohalosilane synthesis using this direct synthesis process ever since it was invented. That is, organochlorosilanes such as methylchlorosilane are synthesized by the Rochow reaction in which an organic halide such as an alkyl halide (e.g., methyl chloride) or a halogenated aryl compound (e.g., halobenzene) is passed through metallic silicon and a catalyst component composed of a copper catalyst and a small amount of co-catalyst to induce a direct reaction in a vapor phase. In this reaction, because the cost of metallic silicon accounts for a large portion of the raw material costs, it is essential to increase the conversion of metallic silicon and also to maintain reaction conditions in such a way as to bring the formation ratio of the many by-products that generally form together with the main product into line with the demand-supply balance for organochlorosilanes. Industrially, the reaction is generally carried out in a reactor such as a fluidized bed reactor, vibrating fluidized bed reactor or stirred tank reactor while adding the catalyst component. Although activation to bring the reaction to a steady state takes a long time, the steady state is relatively shortlived. Accordingly, it is important to minimize the decline in activity (i.e., the rate of decline in the reaction rate and selectivity) due to the accumulation of deactivated catalyst component as the reaction proceeds in order to enable long-term operation, and thereby increase the conversion of metallic silicon to useful silanes.

The aluminum present as an impurity in industrial metallic silicon reportedly has a large impact on the reaction rate and selectivity. For example, according to Norwegian Patent No. 169831, the ternary phase $FeAl_3Si_2$ in silicon provides enhanced reactivity, and the quaternary phase $Fe_4Si_6Al_4Ca$ provides enhanced selectivity. However, the reactivity and selectivity cannot both be increased. That is, it is well known that in the Rochow reaction the aluminum present as an impurity in the industrial metallic silicon serving as one of the starting materials is essential for increasing the catalytic activity, yet it lowers the selectivity for diorganodihalosilanes that are in high demand. The form and reactivity of aluminum present in metallic silicon has been the subject of considerable research and debate.

British Patent No. 2153697 teaches that both the reactivity and selectivity of a direct synthesis process are increased by the use of a copper catalyst comprising a mixture of copper, $Cu_2O$ and CuO, from 200 to 5,000 ppm of a tin-containing compound, and from 50 to 5,000 ppm of aluminum or an aluminum-containing compound. Unfortunately, this approach fails to provide significant increases in reactivity and selectivity.

H.M. Rong has proposed, in Norwegian Patent No. 950760, a process for the production of alkylhalosilanes by reacting elemental silicon with an alkyl halide at an elevated temperature in the presence of a copper-based catalyst and an optional promotor. However, such a process does not achieve significant increases in reactivity and selectivity. Although the examples of aluminum cited in this prior art include metallic aluminum, aluminum alloys, aluminum-containing silicon alloys and solid aluminum-containing compounds, none of these has sufficient activity by itself. Various active forms of these aluminum substances have been proposed, but no accepted view yet exists on their efficacy, nor have any specific procedures been described for activating such aluminum substances.

Thus, although aluminum has been the subject of considerable research, such efforts have involved merely the use of aluminum impurities in metallic silicon by default as the reaction promotor. No art disclosed to date has proposed activating the aluminum in metallic silicon, which is present primarily as aluminum silicide, to put it to effective use. Because the prior art uses as a starting material aluminum-containing metallic silicon, which has both advantages and drawbacks in the Rochow reaction, the concentration of aluminum within the reaction system is difficult to control, as is also the starting material itself.

SUMMARY OF THE INVENTION

It is therefore an object of the invention to provide a process for preparing organohalosilanes by the Rochow reaction that can shorten the time required for activation, increase the selectivity for desired diorganodihalosilanes, prolong the steady state of the reaction and improve conversion of the silicon.

The inventor has found it to be effective, when preparing organohalosilanes by the Rochow process, to add to the reaction system at least one promotor selected from among activated aluminum, activated aluminum alloys and activated aluminum carbide.

As noted above, there is little doubt that at least some of the aluminum present as aluminum alloy within metallic silicon reacts with halogenated hydrocarbons to form aluminum halides. The aluminum halides reportedly react with the oxide film present on the surface of the metallic silicon, inducing a surface-activating effect. Moreover, it has also been reported that the presence of aluminum halides increases the vapor pressure of copper halides that form from the copper catalyst, thus facilitating diffusion of the copper catalyst and ultimately promoting the catalytic effect of the copper. In any case, it appears to be indisputable that the presence of aluminum promotes the reaction.

Yet, at the same time, the aluminum halides that form as by-products are very strong Lewis acids, and are indeed familiar as catalysts for organohalosilane disproportionation reactions. Hence, the presence of excess aluminum halide gives rise to disproportionation within the reaction system of the diorganodihalosilanes which are primary constituents of the reaction product and are preferably obtained in the highest possible yield, resulting in an undesirable increase in silane by-products such as monoorganotrihalosilanes and triorganomonohalosilanes.

More specifically, in the activating reaction stage at the beginning of the Rochow reaction, the formation of much aluminum halide is advantageous because it is necessary to activate the catalyst component, but once a steady state has been reached, the formation of little aluminum halide is preferred. Achieving in this way the mutually conflicting goals of improved reactivity and improved selectivity requires very close and careful control of the reaction, yet the prior art carries out reactions which attempt to achieve this delicate effect using the aluminum impurities already present within the metallic silicon, such as alloys with silicon. Such aluminum impurities within metallic silicon originate from impurities within the silica starting materials used in the metallurgical production process, and so are not uniformly present throughout the metallic silicon. Rather, they form intermetallic compounds with silicon and other metals or compounds with nonmetallic elements, and are dispersed throughout the silicon as impurity zones. The slow rate of aluminum halide formation from reactions with organic halides has made it necessary to take one of two approaches: either use a higher aluminum content than would otherwise be warranted or use metallic silicon having a low aluminum content to achieve good selectivity in an activation period having a long initial stage. Hence, it is impossible in practice to control the active aluminum within the catalyst component to the required level, and such control by itself cannot increase both the reactivity and the selectivity.

Upon investigating instead reactions between what is referred to in the prior art as "active aluminum" and halogenated hydrocarbons, the inventor learned that within a temperature range of 250 to 400° C. such reactions either do not proceed quantitatively (that is, to a sufficient degree) or do not proceed at all. However, when at least one aluminum substance selected from among aluminum, aluminum alloys and aluminum carbide is premixed with the copper compound, the inventor found that the aluminum can be made to react quantitatively with halogenated hydrocarbons within this temperature range to form aluminum halides. This showed that activated aluminum, activated aluminum alloy and activated aluminum carbide have an effective action on the reactivity and selectivity of the reaction. That is, the inventor discovered that aluminum, aluminum alloy and aluminum carbide react quickly with halogenated hydrocarbons in the presence of a copper compound to form aluminum halides and hydrocarbons. Moreover, because the reaction proceeds quantitatively, sufficient activation can be achieved with addition of the minimum required amount of the aluminum substance. The inventor also found that, in the presence of a catalyst composed solely of a copper compound, aluminum carbide and aluminum alloys such as aluminum silicide, which have a much lower reactivity with halogenated hydrocarbons than does metallic aluminum, are activated by the addition of a small amount of co-catalyst (e.g., metallic tin, zinc, antimony, phosphorus, iron) with respect to the copper compound and thus rapidly react to form an aluminum halide. In this reaction as well, because the aluminum present in the form of an alloy or the aluminum carbide reacts quantitatively, sufficient activation of the Rochow reaction can be achieved by adding the aluminum substance in the minimum required amount. Another unanticipated discovery the inventor made was that the activated aluminum, activated aluminum alloy and activated aluminum carbide react more rapidly with methyl halides to form aluminum halides and hydrocarbons, thereby reducing the amount of hydrogen that generally forms as a by-product when conventional aluminum compounds are used. This has the effect of suppressing the formation of organohydrogenhalosilanes (Si-H group-bearing silanes) that are by-products of direct synthesis, thereby resulting in an increased selectivity.

Thus, although the prior art makes no mention of the deliberate use of aluminum as a co-catalyst, the inventor has found the use of quick-acting aluminum to be effective and important in controlling the reactivity of the catalyst component which changes from moment to moment.

Accordingly, the invention provides a process for preparing organohalosilanes comprising the step of reacting metallic silicon with a halogenated hydrocarbon at a temperature of 250 to 400° C. in a stirred tank reactor or a fluidized bed reactor and in the presence of a copper or copper compound catalyst and at least one promotor selected from among activated aluminum, activated aluminum alloy and activated aluminum carbide.

Because the aluminum promotor is independent of impurities in the metallic silicon starting material and quick-acting and because it does not remain or accumulate within the reaction system, the inventive process is able to achieve a reaction having a high selectivity and a high conversion. This in turn makes it possible also to facilitate control of the starting materials.

BRIEF DESCRIPTION OF THE DRAWINGS

FIG. 1 is a schematic showing an organohalosilane production apparatus such as may be used to carry out the process according to the present invention.

FIG. 2 is a graph of the results of thermogravimetric measurements performed on aluminum alloy (AlSi) and activated aluminum alloy in a methyl chloride atmosphere.

FIG. 3 is a graph of the results of differential thermal analysis measurements performed in a methyl chloride atmosphere. The graph illustrates the effects of activated aluminum alloy addition upon a reaction between metallic silicon and copper chloride.

FIG. 4 is a graph of the results of thermogravimetric measurements performed on aluminum and activated aluminum in a methyl chloride atmosphere.

FIG. 5 is a graph of the results of differential thermal analysis measurements performed in a methyl chloride atmosphere. The graph illustrates the effects of activated aluminum addition upon a reaction between metallic silicon and copper chloride.

DETAILED DESCRIPTION OF THE INVENTION

As noted above, the present invention is directed at an organohalosilane preparation process capable of achieving high yield, high selectivity and high conversion. The process is comprised of an organohalosilane direct preparation reaction in which metallic silicon is reacted with a halogenated hydrocarbon at a temperature of 250 to 400° C. in a stirred tank reactor or a fluidized bed reactor. The reaction is carried out in the presence of a copper or copper compound catalyst and at least one promotor selected from among activated aluminum, activated aluminum alloy and activated aluminum carbide.

The activated aluminum, activated aluminum alloy or activated aluminum carbide is able to react fully with halogenated hydrocarbons within a temperature range of 250 to 400° C. to quantitatively form aluminum halide.

The activated aluminum, activated aluminum alloy or activated aluminum carbide can be prepared by the addition and admixture of a copper compound. The aluminum alloy may be any alloy which contains aluminum, although an aluminum-silicon alloy is preferred. If aluminum alloy or aluminum carbide is used, the addition and admixture of a co-activator in addition to the copper compound is especially preferred.

Exemplary copper compounds include cuprous chloride, cupric chloride, cuprous oxide and cupric oxide. The copper compound is added in an amount within a range of 0.1 to 20 wt %, and especially 1 to 10 wt %, based on the aluminum, aluminum alloy or aluminum carbide.

Preferred examples of the co-activator include tin, zinc, phosphorus, antimony, iron, and compounds thereof. The co-activator is preferably added in an amount of 0.01 to 20 wt %, and especially 0.1 to 10 wt %, based on the aluminum alloy or aluminum carbide.

The aluminum, aluminum alloy or aluminum carbide has a particle size of preferably not more than 10 mm, more preferably from 1 micron to 1 mm, and most preferably from 10 microns to 1 mm.

Addition and mixture of the copper compound and co-activator with the aluminum, aluminum alloy or aluminum carbide is preferably carried out by mechanical mixture in a dry atmosphere, and most preferably under strong shear forces.

Aside from the addition of at least one promotor from among the above-described activated aluminum, activated aluminum alloy and activated aluminum carbide, the inventive process for preparing organohalosilanes may be carried out in accordance with a conventional process.

The metallic silicon used as the starting material in the inventive process may be, for example, metallurgical silicon, amorphous silicon for use in solar cells and semiconductor-grade high-purity silicon. Of these, metallurgical silicon is preferred. Impurities in metallurgical silicon include iron, titanium, calcium, aluminum, phosphorus and boron. Such impurities may be present at about the same level as in metallurgical silicon currently in common use. However, to facilitate control of the aluminum concentration and thereby further enhance the advantageous effects of the invention, it is preferable for the metallurgical silicon to be one which has been refined in the metallic silicon production process so as to minimize the level of impurities. Elements which are clearly catalyst poisons or may poison the reaction, such as chromium, nickel, lead and mercury, should be reduced to the lowest possible levels. A particle size within a range of 1 to 500 microns is preferred.

The halogenated hydrocarbon serving as a starting material in the inventive process is preferably an alkyl halide such as methyl chloride, ethyl chloride or propyl chloride, an alkenyl chloride such as vinyl chloride, or a chlorinated aryl compound such as chlorobenzene. Methyl chloride is especially preferred.

Preferred examples of the copper or copper compound used as the catalyst include metallic copper, copper oxides, copper halides such as copper chlorides, carboxylic acid salts of copper such as cupric formate and cupric oxalate, and mixtures thereof. The use of metallic copper, copper oxides or mixtures thereof is especially preferred. The copper or copper compound is preferably used in an amount corresponding to 0.1 to 20 wt % of copper, and especially 1 to 10 wt % of copper, based on the metallic silicon. The copper may be added to the reactor together with the silicon, or it may be mechanically mixed with the silicon beforehand.

The promotor is preferably added to the reactor in an amount corresponding to 0.001 to 1.0 wt % of metallic aluminum, based on the metallic silicon. The amount of addition varies depending on the reaction state, and is most preferably from 0.01 to 0.05 wt %.

In the practice of the invention, an optional promotor such as zinc, antimony, tin, phosphorus or iron may also be added and used together with the aluminum promotor. In addition, an agglomeration inhibitor such as silica, diatomaceous earth or carbon may be used to prevent agglomeration of the catalyst component.

The reaction is carried out at a temperature within a range of 250 to 400° C., and preferably 250 to 350° C.

The reactor is a stirred tank reactor or a fluidized bed reactor. A fluidized bed reactor is preferable for commercial production.

No particular limitation is imposed on the organohalosilane production apparatus. For example, use may be made of an apparatus like that shown in FIG. 1. Referring to FIG. 1, a fluidized bed reactor 1 is connected at the bottom thereof to a starting material hopper 3 via a starting material feed line 2. The metallic silicon, the copper catalyst or a catalyst mixture of the copper catalyst with the co-catalyst, and the promotor are introduced to the bottom of the reactor 1 from the hopper 3 via the feed line 2. An organic halide feed line 4 equipped with a heater 5 is also connected to the bottom of the reactor 1, and introduces to the bottom of the reactor 1 an organic halide gas or vapor so as to form within the reactor 1 a fluidized bed 1a of the metallic silicon and catalyst. The apparatus is also equipped with a cooler 6.

The organic halide gas or vapor is preferably introduced at a linear flow rate of 2 to 10 cm/s under steady-state conditions. The reaction is carried out at 250 to 400° C., and preferably 250 to 350° C.

The organohalosilane formed in the reaction passes through a discharge line 7 connected to the top of the reactor 1, and is introduced into a first cyclone 8, where entrained solid particles are separated off. The solid particles are returned to the fluidized bed 1a via a solid particle return line 9. The organohalosilane then passes to a second cyclone 10, where more entrained solid particles are separated off and stored in a separated particle storage tank 11. Next, the organohalosilane is condensed in a first silane condenser 12, then in a second silane condenser 13, and is collected and stored in a silane storage tank 14. Some or all of the waste gases remaining after the solid particles have been separated off and the organohalosilane has been condensed and removed is returned once again to the reactor 1 through an organic halide return line 16 equipped with a circulating gas-type compressor 15. The return line 16 is connected to the organic halide feed line 4.

In prior-art organohalosilane synthesis reactions involving the reaction of an alkyl halide such as methyl chloride or a halogenated aryl compound such as chlorobenzene with metallic silicon in the presence of a copper catalyst and a co-catalyst such as zinc or tin, 10 commonly referred to as the Rochow reaction, the activation time (induction period) until the silane formation reaction rate and the selectivity reach a steady state is very long, yet the steady state itself is of very short duration. How to resolve this dilemma was a major challenge. The present invention has been arrived at based on a new understanding of the mechanism of action and the physical properties of the aluminum that is present as an impurity in industrialgrade metallic silicon and acts as a co-catalyst in the reaction. This knowledge has made it possible to optimize the form of the aluminum so as to resolve the foregoing problems of the Rochow reaction. By shortening the time required for activation and increasing the selectivity for desirable diorganodihalosilanes in particular, the inventive process prolongs the steady state of the reaction, making it possible to improve conversion of the silicon and in turn enhancing the reaction performance.

EXAMPLE

The following examples, wherein all parts are by weight, are provided to illustrate the invention, and are not intended to limit the scope thereof.

Example 1

One hundred parts of aluminum silicide (AlSi; manufactured by Rare Metallics; average particle size, about 30 $\mu$m) was mixed in a dry atmosphere with 10 parts of cupric chloride containing 10 wt % (tin basis) of tin powder, tin phosphide or tin oxide as a co-activator. The mixtures were thermogravimetrically analyzed while heating at a rate of 5° C./min under a stream of methyl chloride. For the sake of comparison, measurements were carried out under the same conditions using a similar mixture containing no co-activator, and using aluminum silicide powder alone (AlSi$_x$; average particle size, 20 µm). The results are shown in FIG. 2, from which it is apparent that, in the course of a rise in temperature to 590° C., the blank composed solely of aluminum silicide showed no weight loss on heating due to aluminum chlorination and evaporation. The mixture composed of aluminum silicide and the copper compound showed only a slight weight loss starting at a temperature of about 400° C. The aluminum silicide mixtures in which tin, tin phosphide or tin oxide was added as a co-activator showed abrupt and substantially quantitative weight losses starting at a temperature of about 290° C., clearly demonstrating that such mixtures form active aluminum alloys that furnish aluminum chloride having a large reaction promoting effect in the Rochow reaction.

Example 2

One hundred parts of metallic silicon powder of relatively low aluminum content (from Australia; aluminum content, 0.04%; average particle size, 40 µm), 0.02 wt % of activated aluminum silicide (AlSi manufactured by Rare Metallics; average particle size, approx. 30 µm; representing about 0.01 wt % of aluminum) to which had been added 10 wt % (aluminum silicide basis) of cupric chloride catalyst prepared beforehand in dry air so as to include 10 wt % (aluminum silicide basis) of metallic tin powder, and 10 wt % of cupric dichloride were uniformly mixed. The resulting mixture was analyzed while heating at a rate of 4° C./min under a stream of methyl chloride in a gas flow-through type differential thermal analyzer. The results are shown in FIG. 3. For comparison, the results obtained using a similar mixture containing no co-activator are also shown. In FIG. 3, the use of activated aluminum alloy to which a co-activator was added provides a sharp peak on the lower temperature side, from which it is apparent that an active catalyst component has formed. This reaction corresponds to the active site-forming reaction:

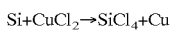

in the Rochow reaction, demonstrating that the presence of activated aluminum alloy results in more effective formation of active sites.

Example 3

An 8 cm diameter steel reactor equipped with a spiral stirrer like that shown in FIG. 1 and thoroughly flushed beforehand with nitrogen was charged with 100 parts of the low-aluminum metallic silicon powder described in Example 2, 6 parts of cupric chloride, 0.5 part of zinc oxide, and 0.2 part or 0.4 part of activated aluminum alloy (prepared by mixing 100 parts of the aluminum silicide AlSi having an average particle size of about 30 µm described in Example 1 with 10 parts of cupric chloride to which 10 wt % of metallic tin powder had been added and mixed beforehand in a dry atmosphere). First, the nitrogen gas was introduced into the reactor at a linear flow rate of 2 cm/s to fluidize the reactor contents and the temperature was raised to 350° C. while stirring with the spiral stirrer. Next, the reaction was effected by gradually adding methyl chloride while controlling the reaction temperature to 280 to 300° C., and the reaction was ultimately continued at a linear flow rate of 7 cm/sec. The reaction was continued for 6 hours, at which point it was brought to completion. Table 1 shows the average rate of silane formation and the composition of the silane that formed during this period. Table 1 also shows, for the sake of comparison, the results obtained for a mixture in which activated aluminum was not included.

TABLE 1

| | Amount of activated aluminum alloy added (pbw) | Rate of silane formation (g/100 g of Si/h) | Me(H)SiCl$_2$ (%) | Me$_2$SiCl$_2$ (%) | MeSiCl$_3$/ Me$_2$SiCl$_2$ ratio |
|---|---|---|---|---|---|
| Example 3-1 | 0.2 | 25.0 | 2.0 | 86.5 | 0.08 |
| Example 3-2 | 0.4 | 31.0 | 1.7 | 83.8 | 0.09 |
| Comparative Example 1 | 0.0 | 6.5 | 4.5 | 83.7 | 0.11 |

Example 4

One hundred parts of metallic aluminum particles (average particle size, about 500 µm) was mixed with 10 parts of cuprous chloride or cupric chloride in a dry atmosphere. The mixture was thermogravimetrically analyzed while heating at a rate of 5° C./min under a stream of methyl chloride. For the sake of comparison, metallic aluminum (average particle size, about 500 µm) alone and aluminum silicide powder (AlSi$_x$; average particle size, 20 µm) alone were each measured under the same conditions. The results are shown in FIG. 4. As is apparent from FIG. 4, up to a temperature of 600° C., the blank composed solely of metallic aluminum showed no weight loss on heating due to aluminum chlorination and evaporation. Even in the case of aluminum silicide alone, only a very small weight loss was observed at 593° C. By contrast, the systems composed of cuprous chloride or cupric chloride added to metallic aluminum showed a dramatic weight loss near 400° C. (with sufficient activity being noted even below 400° C.). Hence, active aluminum clearly formed in the Rochow reaction.

Example 5

One hundred parts of metallic silicon powder of low aluminum content (from Australia; aluminum content, 0.04%; average particle size, 40 µm), 1 part of activated aluminum prepared beforehand by the mixture of 10 parts of cupric chloride with 100 parts of metallic aluminum powder (average particle size, about 500 µm) in a dry atmosphere, and 10 parts of cupric chloride were uniformly mixed. The resulting mixture was analyzed at a heating rate of 4° C./min under a stream of methyl chloride in a gas flow-through type differential thermal analyzer. The results are shown in FIG. 5. For comparison, FIG. 5 also shows the results obtained using a mixture of the above-described metallic silicon powder with 10 parts of cupric chloride to which activated aluminum was not added. In FIG. 5, a sharp peak appears for the mixture containing activated aluminum, from which it is apparent that an active catalyst component has formed. This reaction corresponds to the active site-forming reaction:

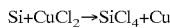

in the Rochow reaction, demonstrating that the presence of activated aluminum results in more effective formation of active sites.

Example 6

An 8 cm diameter steel reactor equipped with a spiral stirrer like that shown in FIG. 1 and thoroughly flushed beforehand with nitrogen was charged with 100 parts of the low-aluminum metallic silicon powder described in Example 5, 6 parts of cupric chloride, 0.5 part of zinc oxide, and 0.1 part or 0.2 part of activated aluminum (prepared by mixing 100 parts of the metallic aluminum particles having an average particle size of about 500 μm described in Example 4 with 10 parts of cupric chloride in a dry atmosphere). First, the nitrogen gas was introduced into the reactor at a linear flow rate of 2 cm/s to fluidize the reactor contents and the temperature was raised to 350° C. while stirring with the spiral stirrer. Next, the reaction was effected by gradually adding methyl chloride while controlling the reaction temperature to 280 to 300° C., and the reaction was ultimately continued at a linear flow rate of 7 cm/sec. The reaction was continued for 6 hours, at which point it was brought to completion. Table 2 shows the average rate of silane formation and the composition of the silane that formed during this period. Table 2 also shows, for the sake of comparison, the results obtained for a mixture in which activated aluminum was not included.

TABLE 2

| | Amount of activated aluminum alloy added (pbw) | Rate of silane formation (g/100 g of Si/h) | Me(H)SiCl$_2$ (%) | Me$_2$SiCl$_2$ (%) | MeSiCl$_3$/ Me$_2$SiCl$_2$ ratio |
|---|---|---|---|---|---|
| Example 6-1 | 0.1 | 21.0 | 2.8 | 84.5 | 0.09 |
| Example 6-2 | 0.2 | 33.0 | 3.0 | 82.1 | 0.10 |
| Comparative Example 1 | 0.0 | 6.5 | 4.5 | 83.7 | 0.11 |

Japanese Patent Application No. 2000-034646 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An organohalosilane preparation process comprising the reaction of metallic silicon with a halogenated hydrocarbon at a temperature of 250 to 400° C. in a stirred tank reactor or a fluidized bed reactor, wherein the reaction is carried out in the presence of a copper or copper compound catalyst and at least one promoter comprising activated aluminum, activated aluminum ally or activated aluminum carbide which are prepared beforehand by mixing metallic aluminum, aluminum alloy or aluminum carbide with 0.1 to 20 wt % of a copper compound, based on the aluminum, aluminum alloy or aluminum carbide, said activated aluminum, activated aluminum alloy and activated aluminum carbide capable to react with halogenated hydrocarbons within a temperature range of 250 to 400° C. to quantitatively form aluminum halide.

2. A process according to claim 1, wherein the activated aluminum is prepared beforehand by mixing metallic aluminum with 0.1 to 20 wt % of a copper compound, based on the aluminum.

3. A process according to claim 2, wherein the copper compound is cuprous chloride, cupric chloride, cuprous oxide or cupric oxide.

4. A process according to claim 1, wherein the activated aluminum alloy comprises 0.01 to 20 wt % of a copper compound and 0.01 to 20 wt % of a co-activator, based on the aluminum alloy.

5. A process according to claim 4, wherein the copper compound is cuprous chloride, cupric chloride, cuprous oxide or cupric oxide, and the co-activator is tin, zinc, phosphorus, antimony, iron or a compound thereof.

6. A process according to claim 1, wherein the activated aluminum carbide comprises 0.01 to 20 wt % of a copper compound and 0.01 to 20 wt % of a co-activator, based on the aluminum carbide.

7. A process according to claim 6, wherein the copper compound is cuprous chloride, cupric chloride, cuprous oxide or cupric oxide, and the co-activator is tin, zinc, phosphorus, antimony, iron or a compound thereof.

8. A process according to claim 1, wherein the promotor is used in an amount corresponding to 0.001 to 1.0 wt % of aluminum, based on the metallic silicon.

9. An organohalosilane preparation process comprising the reaction of metallic silicon with a halogenated hydrocarbon at a temperature of 250 to 400° C. wherein the reaction is carried out in the presence of a copper or copper compound catalyst and at least one promoter comprising activated aluminum, activated aluminum ally or activated aluminum carbide, wherein the at least one activated aluminum, activated aluminum alloy and activated aluminum carbide capable to react with halogenated hydrocarbons to quantitatively form aluminum halide.

* * * * *